United States Patent

Takao et al.

Patent Number: 5,320,674
Date of Patent: Jun. 14, 1994

[54] ULTRAVIOLET RAY SCREENING AGENT

[75] Inventors: Yuji Takao; Akitsugu Ando; Tetsusi Kosugi, all of Toyohashi; Fukuji Suzuki, Yokohama; Kazuhisa Ohno, Yokohama; Katsuki Ogawa, Yokohama, all of Japan

[73] Assignees: Topy Industries, Limited; Shiseido Company, Ltd., both of Tokyo, Japan

[21] Appl. No.: 939,948

[22] Filed: Sep. 2, 1992

[30] Foreign Application Priority Data

Sep. 4, 1991 [JP] Japan .................. 3-281839
Sep. 4, 1991 [JP] Japan .................. 3-281840

[51] Int. Cl.$^5$ .................. C04B 14/20; C01B 33/00
[52] U.S. Cl. .................. 106/418; 106/417; 473/328.3
[58] Field of Search .................. 106/417, 418; 423/328.3

[56] References Cited

U.S. PATENT DOCUMENTS

| | | | |
|---|---|---|---|
| 4,067,819 | 1/1978 | Daimon et al. | 106/417 |
| 5,023,065 | 6/1991 | Ohno et al. | 423/332 |
| 5,094,852 | 3/1992 | Ohno et al. | 106/417 |

FOREIGN PATENT DOCUMENTS 300047  1/1989  European Pat. Off.

*Primary Examiner*—Helene Klemanski
*Attorney, Agent, or Firm*—Armstrong, Westerman, Hattori, McLeland & Naughton

[57] ABSTRACT

A composite synthetic mica powder having an excellent ultraviolet ray screening effect, the composite synthetic mica powder comprising a fine particle layer (B) containing one or more types of elements selected from the group of Te, Bi, Pb, Ce, Fe, Mo, Nb, W, Sb, Sn, V, Mn, Ni, Co, Zn and Ti is formed on the surface of scale-like mica particles (A). The covering ratio of particles (A) by particles (B) is in the range of 0.5 to 1; the ratio of particle size of the particles (B) to plane direction diameter of the particles (A) is 0.1 or less; and particle size of the particles (A) is 1 to 100 μm. Also, a red synthetic mica which develops light-resistant red color closer to the color of human skin and ultraviolet rays, a method for manufacturing the same, and an ultraviolet ray screening agent which contains the synthetic mica. The synthetic mica is expressed by the following formula (I):

$$X_{1\sim1}Y_{2\sim3}(Z_4O_{10})F_{2\times0.75\sim2\times0.99} \qquad (I)$$

where X represents one or more ions selected from the group of Na, K, Li, Ca, Rb and Sr; Y represents one or more ions selected from the group of Mg, Fe, Ni, Mn, Al, Li, Co, Ti and Zn; Z represents one or more ions selected from the group of Al, Si, Ge, Fe, B, Co and Ti; and at least one of Y and Z represents an iron ion; and the molar number of iron contained in the synthetic mica is 0.01 to 3 mols.

7 Claims, 4 Drawing Sheets

ULTRAVIOLET RAY SCREENING AGENT

BACKGROUND OF THE INVENTION

The present invention relates to composite mica powder and new red synthetic mica to be used as base material for paint, ink, coating agent, plastic, film, fiber, glass, and glaze, and also to an ultraviolet ray screening agent containing said mica powder.

Mica powder is used as a filling material for plastics and paint or as pigment for cosmetic products. Also, a mica product having interference color and with its surface covered with an oxide having high refractive index such as titanium oxide is known as "pearl mica".

On the other hand, as means for screening ultraviolet rays, methods are known such as a method for screening ultraviolet rays by scattering effect of particles and a method to absorb ultraviolet ray energy and to convert it to thermal energy. A typical example of the former is to use titanium oxide, and this is used as an ultraviolet ray scattering agent in cosmetic products, plastics, etc. As the material for the latter, an ultraviolet ray absorbing agent having benzophenone and the like as principal component is known. In addition, a large number of ultraviolet ray screening agents have been proposed. For example, there are composite oxides of metal such as aluminum and zinc (Japanese Patent Laid-Open Publication No. 62-275182), zirconia particle containing cerium (Japanese Patent Laid-Open Publication No. 2-135275), etc. Also, an ultraviolet ray absorbing agent containing mica has also been proposed. For example, there is a product having nickel-containing synthetic mica as main component (Japanese Patent Laid-Open Publication No. 58-19379), a product having synthetic mica containing Te and the like as main component (Japanese Patent Laid-Open Publication No. 3-33179), etc. Also, an ultraviolet ray screening pigment has been proposed (Japanese Patent Laid-Open Publication No. 62-187770), which is covered with titanium oxide in such quantity that pearl luster due to interference does not virtually appear on mica surface.

On the other hand, mica has been widely used for cosmetic products because it has excellent transparent property, luster and high extensibility. In recent years, not only natural mica but also synthetic mica have been developed as an additive for cosmetic products (Japanese Patent Laid-Open Publication No. 63-241072).

The mica powder of a conventional type has been used as scale-like particles of about 1 to 500 μm after being pulverized by a dry or wet type pulverizing method. This conventional type mica powder is disadvantageous in that it can utilize only the heat-resistant and insulating properties of the mica powder. For this reason, the ultraviolet ray absorbing function is provided by giving interference color through adoption of a particle structure covered with titanium oxide as in the case of the pearl mica described above or by a method to replace the elements in mica with other elements through synthesis. However, the pearl mica covered with titanium oxide can give interference color, but it has no transparency specific to mica, or titanium oxide has poor resistance to light. The ultraviolet ray absorbing mica which contains specific elements does not have sufficient effect to screen ultraviolet rays.

In a ultraviolet ray screening agent, the ultraviolet ray scattering agent such as titanium oxide has excellent effect to screen ultraviolet rays while it impairs transparency of mica because it also scatters visible rays, and this is not suitable for the application where transparency is required. In case it is blended in cosmetic products, the white color is exaggerated and gives an unnatural impression. On the other hand, an organic type ultraviolet ray absorbing agent has outstanding ultraviolet ray absorbing potency within a specific wavelength range, but it has poor weatherproof property and lacks stability.

As natural mica, muscovite, phlogopite, and biotite are known, and these are grayish white to blackish brown in color. Mica can be synthesized by various methods, and it is known that mica haring an outstanding white color can be obtained from synthesis and that colored synthetic mica can be produced by coordinating colored elements in the crystal structure.

On the other hand, mica is widely used in cosmetic products because it has a high transparent property, luster and extensibility in use. In recent years, not only natural mica but also synthetic mica has been developed as an additive for cosmetic products. For example, the Japanese Patent Laid-Open Publication No. 63-241072 discloses a synthetic mica powder, in which less fluorine ions are eluted and which has a low surface activity and a high oil impregnation properties.

As described above, mica has not been used widely because color cannot be given to it, and despite of its excellent property, only the properties such as insulating property or leafing property coming from its scale-like shape can be utilized. In the fields of paints, plastics, cosmetic products, etc., there are strong demands on a material, which is red in color and has ultraviolet ray screening effect to improve the durability of organic substances. To give red color, however, it is necessary to add a coloring agent such as an organic dye or iron oxide. Because organic dye has low resistance to light and iron oxide contains particles with high refractive index, it is likely to cause unevenness and impairs the transparency important to cosmetic products. On the other hand, an ultraviolet ray scattering agent such as titanium oxide or an organic type ultraviolet ray absorbing agent are used in cosmetic products to defend against ultraviolet rays. Although an ultraviolet ray scattering agent has excellent effect to screen ultraviolet rays, it also scatters visible rays. This leads to impairment of transparency and causes choking and whitening of cosmetic products. An organil type ultraviolet ray absorbing agent has outstanding ultraviolet ray absorbing potency within a specific wavelength range but has poor weatherproof property.

SUMMARY OF THE INVENTION

It is an object of the present invention to provide composite mica powder which has excellent ultraviolet ray screening effect due to the scattering action of mica particles.

It is another object of the present invention to provide composite mica powder which has a high ultraviolet ray screening potency but also a bright external appearance when blended in cosmetic products and is also superb in usability and workability.

To attain the above objects, the present inventors have studied with strenuous efforts and found that, by forming synthetic mica particles having an ultraviolet ray absorbing potency on the mica surface, an excellent ultraviolet ray screening effect is obtained because ultraviolet rays are scattered when said synthetic mica particles absorb ultraviolet rays.

Specifically, the present invention provides composite mica powder and an ultraviolet ray screening agent containing said mica powder, said mica powder comprising a mica particle layer (B) containing one or more types of elements selected from a group of Te, Bi, Pb, Ce, Fe, Mo, Nb, W, Sb, Sn, V, Mn, Ni, Co, Zn and Ti on a surface of the mica particle (A), whereby:

the covering ratio of the above particle (A) by the above (B) is equal to or lower than 1 and is equal to or higher than 0.5;

the ratio of particle size of the above (B) to particle size of the above (A) is higher than 0 and is equal to or lower than 0.1; and particle size of the above (A) is 1 to 100 μm.

The above covering ratio can be calculated by the sum of a projected area of the particle (B) divided by a projected area of the particle (A). Each of the projected areas can be determined under a scanning electron microscope.

The particle size of the above (A) or (B) is:

$$\frac{\text{short axis} + \text{long axis}}{2}$$

of the particle observed under scanning electron microscope.

It is an object of the present invention to provide a new a red synthetic mica which develops red color close to the color of human skin and which effectively screens ultraviolet rays.

It is still another object of the present invention to provide a new red synthetic mica which has a transparent property, has a bright red color with resistance to light and is suitable for use in cosmetic products, in particular, in a foundation.

To attain the above objects, the present inventors have studied with efforts and have found that, through heat treatment of a synthetic mica having a molar number of iron of 0.01 to 3 mols at a specific temperature, a new type of synthetic mica can be obtained, which has a bright red external appearance not seen in conventional type synthetic mica and has a very high ultraviolet ray screening potency.

Specifically, the present invention provides a red synthetic mica, a method for manufacturing said mica and an ultraviolet ray screening agent containing said mica, which is expressed by the following formula (I):

$$X_{1\sim}Y_{2\sim3}(Z_4O_{10}) F_{2\times0.75\sim2\times0.99} \quad (I)$$

(where X represents an ion of one or more types selected from a group of Na, K, Li, Ca, Rb and Sr; Y represents an ion of one or more types selected from a group of Mg, Fe, Ni, Mn, Al, Li, Co, Ti and Zn; Z represents an ion of one or more types selected from a group of Al, Si, Ge, Fe, B, CO and Ti; and at least one of Y or Z contains iron ion), molar number of iron contained in said synthetic mica is 0.01 to 3 mols; and when the synthetic mica is measured by powder cell method, the color in the CIE 1976 (L*a*b*) space is: L*=55 to 75, a*=5 to 20, and b*=5 to 20.

The above and other objects and advantageous features of the invention will become more apparent from the following description.

DETAILED DESCRIPTION OF THE PREFERRED EMBODIMENTS

The mica particle (A) used in the present invention is one or more types of mica, which are selected from a group of natural muscovite, phlogopite, biotite, sericite and synthetic mica. Among these, it is preferable to use mica which contains one or more elements selected from the group of Te, Bi, Pb, Ce, Fe, Mo, Nb, W, Sb, Sn, V, Mn, Ni, Co, Zn and Ti. Particle diameter of the mica particle (A) is 1 to 100 μm.

Mica fine particle (B) used in the present invention must be mica, which contains one or more types of elements selected from a group of Te, Bi, Pb, Ce, Fe, Mo, Nb, W, Sb, Sn, V, Mn, Ni, Co, Zn and Ti. The mica fine particles not containing these elements cannot provide a high effect for screening ultraviolet rays. The shape of the mica fine particles (B) is not specified, but it is preferable that particle size is 1 μm or less, preferably, 0.5 μm or less, or more preferably 0.1 μm or less.

The composite mica powder of the present invention must contain a mica fine particle layer (B) which is formed in such a manner that the covering ratio of the above particle (A) by the above particle (B) is lower than or equal to 1 and higher than or equal to 0.5, that the ratio of particle size of the above (B) to particle size of the above (A) is higher than 0 and lower than or equal to 0.1, and that the particle size of the above (A) is 1 to 100 μm. If not within this range, the covering of the mica fine particle layer (B) is not sufficient, and a satisfactory ultraviolet ray effect is not obtained. In case the particle size (B) is larger than the particle size of (A), the particles (B) may not be attached in a radial direction.

To form the mica fine particle layer (B), the mica fine particles to be formed may be attached in a particle state or may be firmly fixed by sintering or by fusion.

Next, a description will be given on a method to produce the composite mica powder.

To obtain the composite mica powder of the present invention, mica fine particles (B) pulverized to 1 μm or less by a wet type or dry type pulverizer and natural or synthetic mica particles (A) with particle size of 5 to 100 μm are selected so that the ratio of particle size of the above (B) to particle size of the above (A) is higher than 0 and is lower than or equal to 0.1, and these particles are mixed homogeneously by a V type mixer. Then, mica fine particle layer (B) is formed on the surface of mica particles (A) by a mechano-chemical reactor such as Ang mill (manufactured by Hosokawa Micron) or medium type pulverizer such as ball mill so that the covering ratio of the above (A) by the above (B) is lower than or equal to 1 and higher than or equal to 0.5. In this case, better results can be obtained if the mica fine particles (B) not formed on the surface of the mica particles (A) are removed by classifying.

The composite mica powder thus prepared can be foliated by treating with an acid or a chelating agent. Thus, a mica powder with a low surface activity and a good oil impregnation property suitable for cosmetic products can be obtained.

For the above treatment, inorganic and organic acids may be used. As the inorganic acids, there are, for example, hydrochloric acid, nitric acid, sulfuric acid, chloric acid, perchloric acid, periodic acid, bromic acid, phosphoric acid, boric acid and carbonic acid. As the organic acids, there are carboxylic acids such formic acid, acetic acid, acrylic acid, benzoic acid, oxalic acid, malonic acid, succinic acid, glutaric acid, adipic acid, pimelic acid and phthalic acid, oxycarboxylic acids such as lactic acid, malic acid, tartaric acid and citric acid, and amino acids such as glycine, alanine, valine, leucine, thyrosine, threonine, serine, proline, tryptophan, methionine, cystine, thyroxine, asparagine, glutamic acid, lysine, and arginine. As chelating agents, there are ethylenediaminetetraacetic acid, nitrilotriacetic acid, 1,2-diaminocyclohexanetetraacetic acid, N-oxyethylethylenediamine-triacetic acid, ethleneglycol-bis-tetraacetic acid, ethylenediamine-tetrapropionic acid, etc.

The mica fine particles (B) formed on the surface may be sintered or fused through a heat treatment at 700° to 1200° C. By this heat treatment, mica particles (A) can be turned to particles in the form of a hexagonal plate. The processing by the above acids or chelating agents and the heat treatment may be simultaneously performed.

In an alternative method for manufacturing composite mica powder of the present invention, mica powder containing one or more types of elements selected from a group of Te, Bi, Pb, Ce, Fe, Mo, Nb, W, Sb, Sn, V, Mn, Ni, Co, Zn and Ti is processed by a rotary pulverizer, pulverizing by friction of mica particles themselves and adding solvent such as water by about 10 to 40%. By this procedure, composite mica powder can be obtained by forming fine particle mica containing one or more types of elements selected from the group of Te, Bi, Pb, Ce, Fe, Mo, Nb, W, Sb, Sn, V, Mn, Ni, Co, Zn and Ti on the surface of mica particles. The composite mica powder thus prepared can be treated by the acids or the chelating agents as described above, or by heat treatment at 700° to 1200° C. or by combining both methods.

The composite mica powder of the present invention can be used alone or can be blended and mixed with a cosmetic pigment, coloring pigment, ultraviolet ray scattering agent and ultraviolet ray absorbing agent.

As cosmetic pigments usable in the present invention, there are talc, kaolin, mica, calcium carbonate, magnesium carbonate, magnesium silicate, silicic anhydride, barium sulfate, nylon powder, polyethylene powder, polystyrene powder, etc. As coloring pigments, there are iron oxide, ultramarine blue, chromium oxide, Prussian blue, carbon black, etc. As ultraviolet ray scattering agents, there are titanium oxide, titanium oxide ultra-fine particle, zinc oxide, etc. As ultraviolet ray absorbing agents, there are benzophenone type and benzotriazole type ultraviolet ray absorbing agents.

It is preferable to blend the composite mica powder by about 1 to 100%, and the blending ratio should be selected according to the intended purpose, property, etc. of the products.

It is known that synthetic mica containing Te and the like has effect to absorb ultraviolet rays (Japanese Patent Laid-Open Publication 3-33179). The present invention is based on the findings that, by forming fine particles of synthetic mica having such ultraviolet ray absorbing potency, an ultraviolet ray screening effect can be obtained due to the unexpected ultraviolet ray scattering effect of the mica fine particles. When synthetic mica is simply turned to fine particles, problems occur such as coarsening of particles by secondary aggregation or difficulty of homogeneous dispersion to material, and it is not possible to obtain a high ultraviolet ray screening effect as in the composite mica powder of the present invention. If the particle size ratio is higher than the specified value, the covering is insufficient, and the high ultraviolet ray screening effect as in the present invention cannot be obtained. Through study of the particle structure of mica powder, the present inventors have been found that, by forming the mica fine particles with a specific particle size ratio on the surface of mica particles, a composite mica powder can be obtained which can solve the above problems and which can provide an excellent ultraviolet ray screening effect.

The red mica of the present invention must contain Fe, and synthetic mica not containing Fe is not turned to red.

The molar number of Fe contained in the synthetic mica of the present invention is 0.01 to 3 mols, preferably 0.1 to 2 mols, or more preferably, 0.2 to 1 mol. If it is less than 0.01 mol, the red color is too weak. If it exceeds 3 mols, the mica crystals become poor in quality. In the general formula (I) as shown above, Fe is at octahedron position given by Y, and at tetrahedron position given by Z. The more the molar number of Fe at the octahedron position is, the more the color of the mica is turned to red. Thus, it is necessary in the present invention that iron is contained in the crystal structure. Mere attachment on the mica surface does not provide the effect of the present invention.

As shown in the above general formula of the red mica of the present invention, the molar number of fluorine in the synthetic mica must be 75 to 99% of stoichiometric composition of synthetic mica, preferably 80 to 97.5%, and more preferably 90 to 95%. If it is less than 75%, it is not turned to synthetic mica. If it exceeds 99%, it is not turned to red.

The new red mica of the present invention is synthetic mica expressed by the following formula (II):

$$X_{\frac{1}{2} \sim 1} Y_{2 \sim 3} (Z_4 O_{10}) F_2 \quad (II)$$

(where X represents one or more types of ions selected from a group of Na, K, Li, Ca, Rb and Sr; Y represents one or more types of ions selected from a group of Mg, Fe, Ni, Mn, Al, Li, Co, Ti and Zn; Z represents one or more types of ions selected from a group of Al, Si, Ge, Fe, B, Co, and Ti; and at least one of Y and Z represents an iron ion), and it is produced from synthetic mica with a molar number of Fe contained in the synthetic mica at 0.01 to 3 mols through heat treatment at 600° to 1200° C.

The raw material synthetic mica as expressed by the above formula (II) can be synthesized by a hydrothermal method, a solid a phase reaction method, a fused synthetic method, etc. The mica thus synthesized is pulverized to powder of about 0.1 to 100 μm through a wet type or dry type pulverization. After treating the mica powder with an aqueous solution of one or more types of acids or chelating agents, it is processed by heat treatment at 600° to 1200° C., and the red scale-like mica of the present invention can be produced.

As the acids to treat mica powder, inorganic acids or organic acids may be used. As the inorganic acids, there are hydrochloric acid, nitric acid, sulfuric acid, chloric acid, perchloric acid, periodic acid, bromic acid, phosphoric acid, boric acid and carbonic acid. As the organic acids, there are carboxylic acids such as formic acid, acetic acid, acrylic acid, benzoic acid, oxalic acid, malonic acid, succinic acid, glutaric acid, adipic acid, pimelic acid and phthalic acid, oxycarboxylic acids such as lactic acid, malic acid, tartaric acid, citric acid, etc., and amino acids such as glycine, alanine, valine, leucine, thyrosin, threonine, serine, proline, tryptophan, methionine, cystine, thyroxine, asparagine, glutamic acid, lysine, and arginine.

As chelating agents, there are ethylenediaminetetraacetic acid, nitrilotriacetic acid, 1,2-diaminocyclohexanetetraacetic acid, N-oxyethylethylenediamine-triacetic acid, ethyleneglycol-bis-tetraacetic acid, ethylenediaminetetrapropionic acid, etc.

The time and temperature for treating the mica powder by acids or chelating agents may be properly selected according to the types and concentration of acids or chelating agents. In general, the treating time may be several minutes to several days, and the treating temperature may be 0° to 100° C. The concentration of the treating aqueous solution is preferably 0.05 to 10 mols/liter. For example, when the treating is performed at 20° C. using 0.1N hydrochloric acid, it is preferable that the processing time is 30 minutes to 5 hours.

As the processing methods, method using an agitator, or other known methods using aeration and dipping may be used.

Heat treatment temperature is 600° to 1200° C., or preferably 900° to 1100° C. If it is lower than 600° C., the mica is not turned to red. If it exceeds 1200° C., it is not turned to red and the mica is decomposed.

The time for the heat treatment may be several seconds to several days and may be properly selected according to the heat treatment temperature. For example, when fluorine phlogopite containing 0.2 mol of Fe at the octahedron position is used as a raw material, it is preferable to treat at 1000° C. for 0.5 to 10 hours.

As the heat treatment atmosphere, a oxidation atmosphere, a reduction atmosphere, an argon gas atmosphere, a $N_2$ atmosphere, an ammonia gas atmosphere or a vacuum may be used alone or in combination, and this may be selected properly according to the application, function, etc. of the synthetic mica.

As the heat treatment equipment, any type of the furnaces already known such as a gas furnace, an electric furnace, a rotary kiln, a batch furnace, etc. may be used.

The red mica expressed by the formula (I) of the present invention can be blended and mixed with a cosmetic pigment, a coloring pigment, an ultraviolet ray scattering agent and an ultraviolet ray absorbing agent to prepare an ultraviolet ray agent.

As the cosmetic pigments to be used in the present invention, there are talc, kaolin, mica, calcium carbonate, magnesium carbonate, magnesium silicate, silicic anhydride, barium sulfate, nylon powder, polyethylene powder, polystyrene powder, etc. As the coloring pigments, there are iron oxide, ultramarine blue, chromium oxide, Prussian blue, carbon black, etc. As the ultraviolet ray scattering agents, there are titanium oxide, titanium oxide ultra-fine particles, zinc oxide, etc. As the ultraviolet ray absorbing agents, there are benzophenone type or benzotriazole type ultraviolet ray absorbing agents.

It is preferable to blend the red mica given by the formula (I) by 1 to 100%, and the blending ratio should be properly selected according to each application, property etc.

As an invention relating to the present invention, the Japanese Patent Laid-Open Publication No. 2-289417 discloses an ultraviolet ray absorbing synthetic mica, which contains Fe (converted to $Fe_2O_3$) by 2 to 18 weight %, bivalent Fe (converted to FeO) by less than 0.8 weight %, and in which weight ratio of FeO-converted value to the sum of FeO-converted value and $Fe_2O_3$-converted value is lower than or equal to 0.1, i.e. ($FeO/FeO+Fe_2O_3 \leq 0.1$).

However, the synthetic mica described in the above patent publication is a synthetic mica with a high whitening degree, and it gives no description of synthetic mica, which is colored in red as in the present invention.

According to Nobutoshi Daimon (Kogyo Kagaku Zasshi, Vol. 55, No. 11), it is described that a Ni-containing mica is a greenish yellow, Mn-containing mica is a brown color, Co-containing mica is a pink or blue color, Fe-containing mica is a greenish black or brown (dark brown) color, and it gives no description of a mica in red color. The results of color determination on the Fe-containing mica in brown color reveal that the value of $a^*$ used as measure for reddening is about $-1$ to $+1$, and this is different from the value of $a^*=5$ to 20 in the case of the red scale-like mica of the present invention.

It has been found in the present invention that mica in a transparent and bright red color can be obtained by placing a specific element at a specific position and by setting the molar number of fluorine and the molar number of Fe ions within specific ranges. Such effects are not anticipated by the prior art as described above.

Next, a detailed description will be given on the features of the present invention in connection of the examples, while the present invention will not be limited to these examples.

EXAMPLE 1

Figure 1:
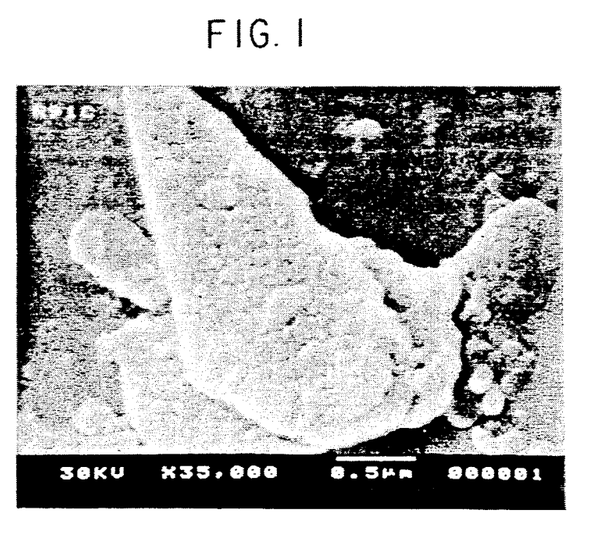
FIG. 1 is an electron micrograph showing the particle structure of a composite mica powder according to the present invention as obtained by Example 1.

A mixture was prepared, which contains potassium silicofluoride by 18.2 w/w %, potassium carbonate by 7 w/w %, magnesium oxide by 28.2 w/w %, aluminum oxide by 11.9 w/w %, and silicon dioxide by 37.0 w/w %. To 100 weight parts of this mixture, 19.0 weight parts of tellurium dioxide were added, and these were mixed for 30 minutes by V type mixer. Next, this mixture was placed in an alumina crucible. After melting the mixture in an electric furance at 1450° C. for 30 minutes, it was cooled down in the furnace. Synthetic tellurium-containing mica thus obtained was pulverized in a ball mill for 48 hours, and 100 parts of mica fine particles containing tellurium of 0.5 μm or less were obtained through centrifugation and classification. To 100 g of the mica fine particles containing tellurium dioxide thus obtained, 100 g of natural mucovite (about 10 μm) was added, and the mixture was processed in a ball mill by mechano-chemical processing for 24 hours, and 195 g of the composite mica powder of the present invention was obtained. This composite mica powder was examined under scanning electron microscope (T-330A; JEOL, Ltd.). The electron micrograph is shown in FIG. 1. The composite mica powder is added to castor oil at 20% concentration. After mixing this in a 3-roll mill, it was coated on a transparent quartz plate in thickness of 10 μm, and UV transmittance at 300 nm was measured using an UV spectrophotometer (U-3210; Shimadzu). As the result, UV transmittance at 300 nm was 15%. Therefore, the UV screening ratio was 85%.

EXAMPLES 2 to 4

To 100 weight parts of a mixture shown in Table 1, a compound given in Table 2 was mixed at a ratio described in Table 2, and the composite mica powder of the present invention was prepared by the same procedure as in the Example 1. On the composite mica powder thus prepared, the UV screening ratio was measured by the same method as in the Example 1. The results are given in Table 3.

Example 5

Figure 2:
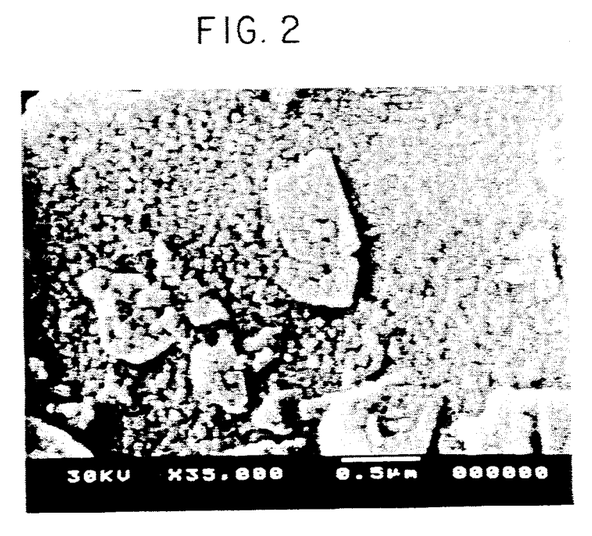
FIG. 2 is an electron micrograph showing the particle structure of a composite mica powder of the present invention as obtained by Example 5.
Figure 5:
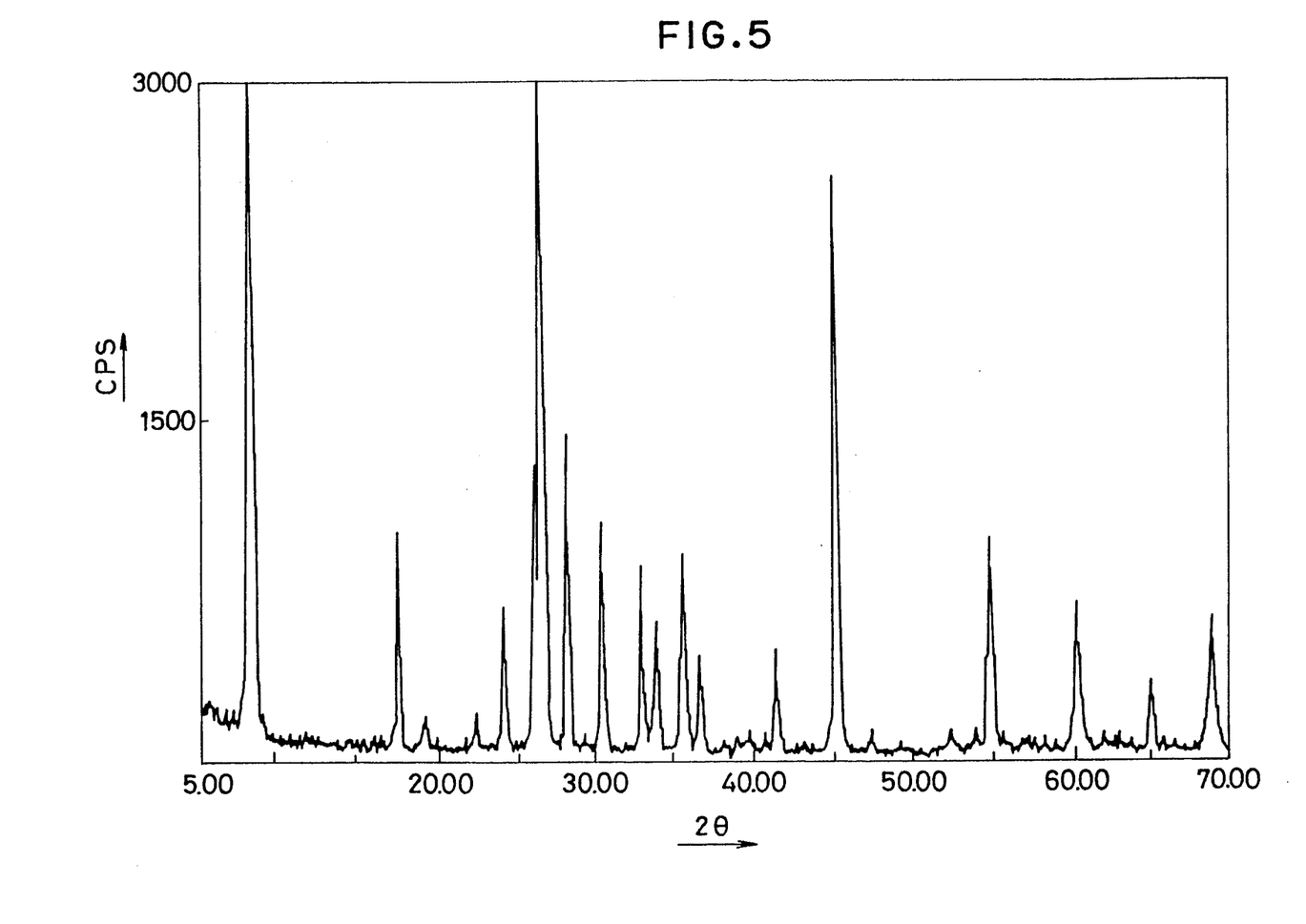
FIG. 5 is an X-ray diffraction chart of a composite mica powder of the present invention as obtained by Example 5.

A mixture was prepared which contains potassium silicofluoride by 19.3 w/w %, potassium carbonate by 5 w/w %, magnesium oxide by 30.0 w/w %, aluminum oxide by 6.3 w/w %, and silicon dioxide by 39.4 w/w %. To 100 weight parts of this mixture, 10 weight parts of iron oxide were added, and this was mixed for 30 minutes by a V type mixer. The mixture thus obtained was placed in an alumina crucible and melted in electric furnace at 1450° C. for 30 minutes and cooled down in the furnace. Thus, 100 parts of synthetic iron-containing mica were obtained. After 200 g of this synthetic mica was pulverized in a ball mill for 48 hours, 100 g of mica fine particles containing iron with particle size of 0.5 μm or less was obtained through centrifugation and classifying. To 100 g of the micro fine particles containing iron thus prepared, 100 g of the above iron-containing synthetic mica (diameter in plane direction: 10 μm) was added, and the mixture was processed for 24 hours in a ball mill through mechano-chemical processing, and 180 g of the composite mica powder of the present invention was obtained. Electron micrograph of this composite mica powder is given in FIG. 2. FIG. 5 shows an X-ray diffraction chart measured by RAD-B (Rigaku Denki-Sha). It complied with ASTM provisions for iron-containing mica according to this X-ray diffraction chart. Further, for the composite mica powder thus prepared, the UV screening ratio was determined by the same procedure as in Example 1. The results are given in Table 3.

EXAMPLES 6 TO 10

To 100 weight parts of the mixture of Table 1, a compound of Table 2 was mixed at a ratio given in Table 2, and the composite mica powder of the present invention was prepared by the same procedure as in the Example 5. On the composite mica powder thus obtained, the UV screening ratio was determined by the same procedure as in Example 1. The results are given in Table 3.

EXAMPLE 11

A mixture was prepared which contains potassium silico-fluoride by 18.2 w/w %, potassium carbonate by 7 w/w %, magnesium oxide by 28.2 w/w %, aluminum oxide by 11.9 w/w % and silicon dioxide by 37.0 w/w %. To 100 weight parts of this mixture, 11 weight parts of vanadium oxide were added, and the mixture was mixed for 30 minutes by V type mixer. Next, this mixture was placed in an alumina crucible. After melting for 30 minutes at 1450° C. in electric furnace, it was cooled down in the furnace. The crystallized mass thus obtained was crushed by an impact crusher to a size of about 100-mesh. 4 kg of vanadium-containing synthetic mica thus obtained and 2 kg of water were placed in an agitator type pulverizer, and after pulverizing it for 96 hours, it was classified, and 1.8 kg of the composite mica powder of the present invention with fine particle mica powder attached on the surface was obtained. On the composite mica powder thus obtained, the UV screening ratio was determined by the same procedure as in Example 1. The results are given in Table 3.

EXAMPLES 12 TO 16

To 100 weight parts of the mixture described in Table 1, a compound given in Table 2 was mixed by a ratio of Table 2, and the composite mica powder of the present invention was produced by the same procedure as in Example 11. On the composite mica powder thus prepared, the UV screening ratio was determined as in Example 1. The results are given in Table 3.

EXAMPLE 17

Figure 3:
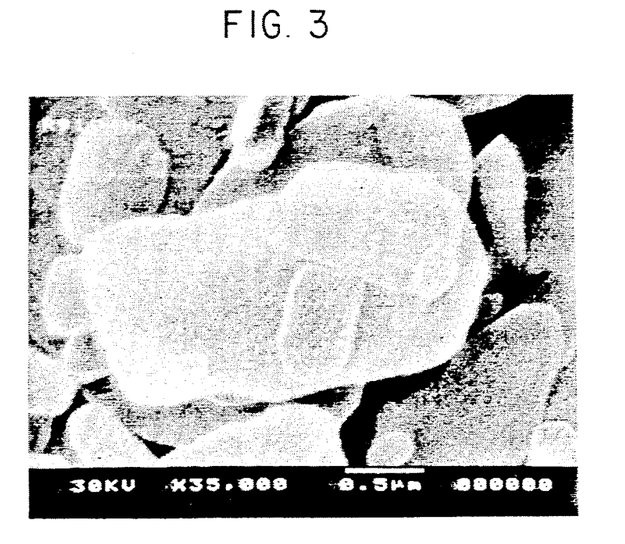
FIG. 3 is an electron micrograph showing the particle structure of a composite mica powder of the present invention as obtained by Example 17.

A mixture was prepared which contains potassium silicofluoride by 19.3 w/w %, potassium carbonate by 5 w/w %, magnesium oxide by 30.0 w/w %, aluminum oxide by 6.3 w/w %, and silicon dioxide by 39.4 w/w %. To 100 weight parts of this mixture, 10.0 weight parts of iron oxide and 10.0 weight parts of titanium oxide were added, and these were mixed for 30 minutes by V type mixer. Then, the mixture was placed in an alumina crucible, melted in electric furnace for 30 minutes at 1450° C. and cooled down in the furnace. The crystal mass thus obtained was crushed to the size of 100-mesh by an impact crusher. 4 kg of synthetic mica powder containing iron and titanium thus prepared and 2 kg of water were placed in an agitator type pulverizer and pulverized for 120 hours. After classifying, 2 kg of the composite mica powder of the present invention with fine particle mica powder attached on the surface was obtained. An electron micrograph of this composite mica powder is shown in FIG. 3. On the composite mica powder thus obtained, the UV screening ratio was determined as in Example 1. The results are shown in Table 3.

EXAMPLE 18

Figure 4:
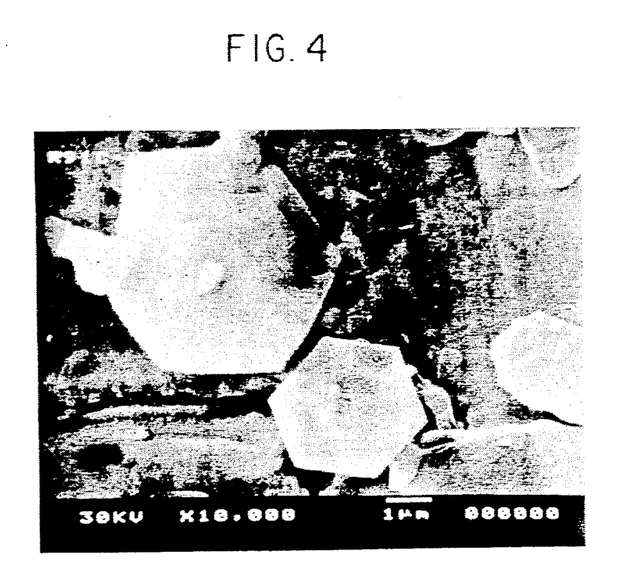
FIG. 4 is an electron micrograph showing the particle structure of a composite mica powder of the present invention as obtained by Example 18.

70 g of the composite mica powder of the present invention as prepared in Example 17 was placed in an alumina crucible. Through heat treatment at 1000° C. for 24 hours in electric furnace, a heat-treated product of the composite mica powder of the present invention was obtained. When the mica fine particles formed on the mica powder surface were examined under an electron microscope, the mica powder was sintered or fused. Also, the composite mica powder was in the form of a hexagonal plate. FIG. 4 shows an electron micrograph of the composite mica powder. On the composite mica powder thus prepared, the UV screening ratio was determined as in Example 1. The results are given in Table 3.

EXAMPLES 19 to 20

To 100 weight parts of the mixture described in Table 1, a compound of Table 2 was mixed at a ratio shown in Table 2, and the composite mica powder of the present invention was produced by the same procedure as in Example 17. On the composite mica powder thus prepared, the UV screening ratio was determined as in the Example 1. The results are given in Table 3.

COMPARATIVE EXAMPLE 1

Mica powder was prepared by the same procedure as in the Example 1 except that tellurium-containing mica fine particles were not used in Example 1. On the mica powder thus obtained, the UV screening ratio was determined as in Example 1. The results are given in Table 3.

COMPARATIVE EXAMPLE 2

Mica powder was obtained by the same procedure as in Example 1, except that iron-containing mica fine particles were not used in Example 5. FIG. 5 shows an electron micrograph of this mica powder. On the mica powder thus obtained, the UV screening ratio was determined as in the Example 1. The results are given in Table 3.

COMPARATIVE EXAMPLE 3

Mica powder was obtained by the same procedure as in Example 19, except that fluorine phlogopite was used instead of iron-containing mica in Example 18. On this mica powder, the UV screening ratio was determined as in Example 1. The results are given in Table 3.

COMPARATIVE EXAMPLE 4

Mica powder was obtained by the same procedure as in Example 1, except that the particle size of tellurium-containing mica fine particles is 2 $\mu$m in Example 1. On the mica powder thus obtained, the UV screening ratio was determined as in Example 1. The results are given in Table 3.

COMPARATIVE EXAMPLE 5

Mica powder was prepared by the same procedure as in Example 11 except that 10 kg of zirconia balls of 5 mm were used in the agitator type pulverizer in Example 11. On the mica powder thus prepared, the UV screen ratio was determined as in Example 1. The results are given in Table 3.

TABLE 1

Mixing ratio of major materials of the mixtures A to F (%).

| Major materials | A | B | C | D | E | F |
|---|---|---|---|---|---|---|
| $K_2SiF_6$ | 18.2 | 19.3 | 20.6 | 19.5 | 21.1 | 19.1 |
| $K_2CO_3$ | 4.7 | 5.0 | 5.3 | 5.1 | 5.5 | 5.0 |
| MgO | 28.2 | 30.0 | 32.0 | 30.3 | 32.8 | 29.6 |
| $Al_2O_3$ | 11.9 | 6.9 | | 12.8 | 13.8 | |
| $SiO_2$ | 37.0 | 39.4 | 42.1 | 32.3 | 26.8 | 46.3 |
| Total | 100 | 100 | 100 | 100 | 100 | 100 |

TABLE 2

Material blending table.

| Example No. | Mixture (weight parts) | | | | | | Compound Type | Weight parts |
|---|---|---|---|---|---|---|---|---|
| | A | B | C | D | E | F | | |
| 1 | 100 | | | | | | $TeO_2$ | 19 |
| 2 | 100 | | | | | | $Bi_2O_3$ | 28 |
| 3 | 100 | | | | | | $PbO_2$ | 28 |
| 4 | 100 | | | | | | $CeO_2$ | 10 |
| 5 | | 100 | | | | | $Fe_2O_3$ | 10 |
| 6 | | | 100 | | | | $MoO_3$ | 38 |
| 7 | 100 | | | | | | $Nb_2O_5$ | 16 |
| 8 | | | | 100 | | | $WO_3$ | 29 |
| 9 | | | | | 100 | | $Sb_2O_3$ | 18 |
| 10 | 100 | | | | | | $SnO_2$ | 18 |
| 11 | 100 | | | | | | $V_2O_5$ | 13 |
| 12 | | | 100 | | | | $MnO_2$ | 10 |
| 13 | | | | | 100 | | NiO | 10 |
| 14 | | | | | 100 | | CoO | 15 |
| 15 | | | | 100 | | | ZnO | 22 |
| 16 | | | | 100 | | | $TiO_2$ | 20 |
| 17 | | 100 | | | | | $Fe_2O_3$ | 10 |
| 18 | | 100 | | | | | $TiO_2$ $CeO_2$ | 10 4 |
| 19 | | | | | 100 | | $Fe_2O_3$ ZnO $TiO_2$ | 10 22 10 |

TABLE 3

Evaluation list.

| | | | Formulation of fine particles | | |
|---|---|---|---|---|---|
| | Type of (A) | Element of (B) | Covering ratio | Particle size ratio | UV screening ratio |
| Example No. | | | | | |
| 1 | Natural muscovite | Te | 0.9 | 0.05 | 85 |
| 2 | Natural muscovite | Bi | 0.9 | 0.04 | 86 |
| 3 | Natural muscovite | Pb | 0.8 | 0.01 | 83 |
| 4 | Natural muscovite | Ce | 0.8 | 0.05 | 80 |
| 5 | Iron-containing synthetic mica | Fe | 0.8 | 0.06 | 85 |
| 6 | Mo-containing synthetic mica | Mo | 0.9 | 0.01 | 81 |
| 7 | Nb-containing synthetic mica | Nb | 0.9 | 0.05 | 85 |
| 8 | W-containing synthetic mica | W | 0.6 | 0.05 | 86 |
| 9 | Sb-containing synthetic mica | Sb | 0.7 | 0.02 | 83 |
| 10 | Sn-containing synthetic mica | Sn | 0.9 | 0.05 | 82 |
| 11 | V-containing synthetic mica | V | 0.6 | 0.03 | 80 |
| 12 | Mn-containing synthetic mica | Mn | 0.9 | 0.04 | 85 |

TABLE 3-continued

| | Type of (A) | Element of (B) | Formulation of fine particles | | UV screening ratio |
| | | | Covering ratio | Particle size ratio | |
| --- | --- | --- | --- | --- | --- |
| 13 | Ni-containing synthetic mica | Ni | 0.5 | 0.06 | 84 |
| 14 | Co-containing synthetic mica | Co | 0.6 | 0.02 | 80 |
| 15 | Zn-containing synthetic mica | Zn | 0.9 | 0.05 | 85 |
| 16 | Ti-containing synthetic mica | Ti | 0.5 | 0.05 | 89 |
| 17 | Fe,Ti-containing synthetic mica | Fe, Ti | 0.9 | 0.03 | 90 |
| 18 | Fe,Ti-containing synthetic mica | Fe, Ti | 1.0 | 0.01 | 90 |
| 19 | Ce,Fe-containing synthetic mica | Ce, Fe | 0.9 | 0.04 | 85 |
| 20 | Zn,Ti-containing synthetic mica | Zn, Ti | 0.8 | 0.05 | 85 |
| Comparative example No. | | | | | |
| 1 | Natural muscovite | None | 0 | 0 | 5 |
| 2 | Iron-containing synthetic mica | None | 0 | 0 | 54 |
| 3 | Fluorine phlogopite | None | 0.9 | 0.05 | 1 |
| 4 | Natural muscovite | Te | 0.8 | 0.2 | 60 |
| 5 | V-containing synthetic mica | V | 0.9 | 0.5 | 60 |

EXAMPLE 21

Figure 6:
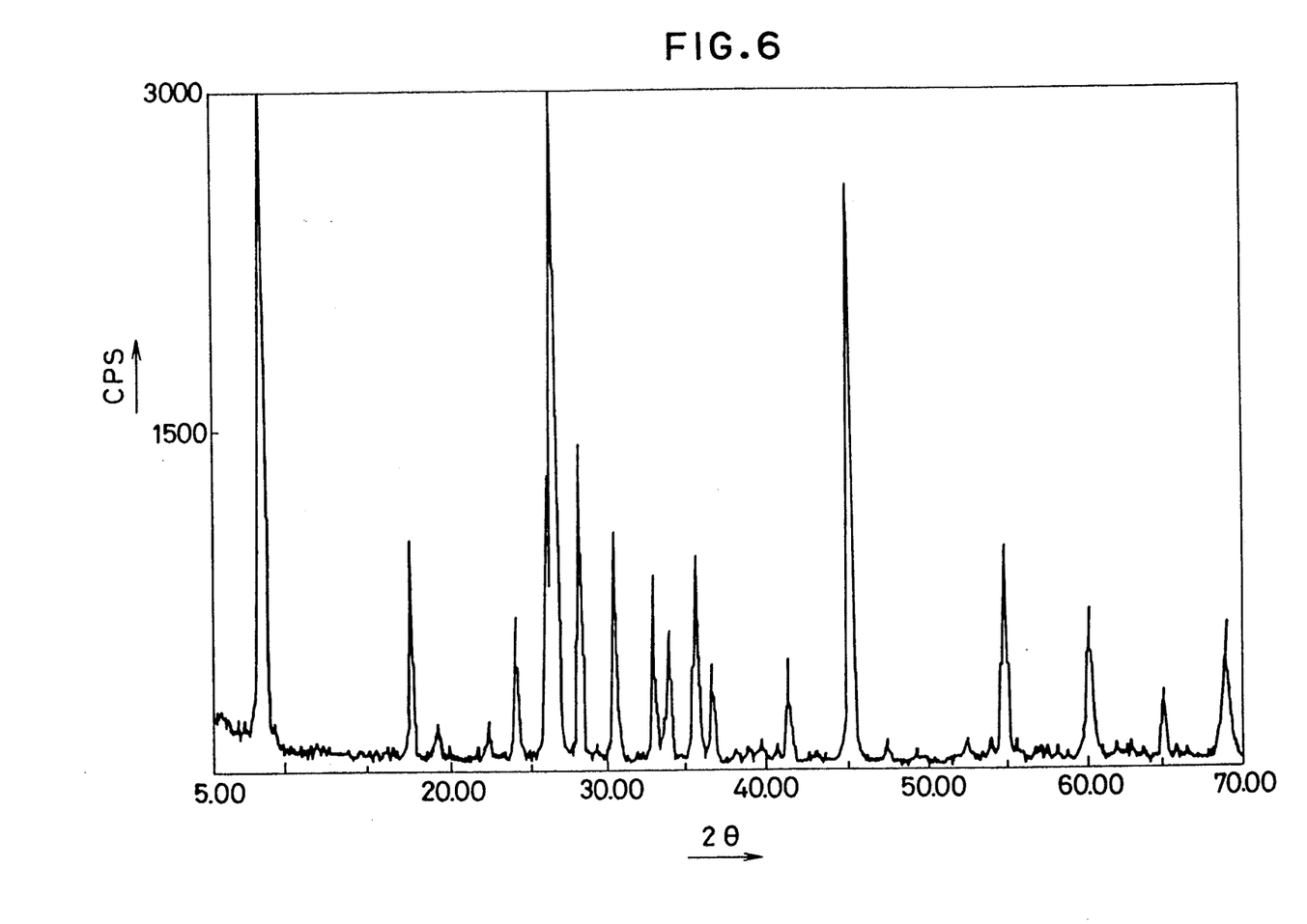
FIG. 6 is an X-ray diffraction chart of a composite mica powder of the present invention as obtained by Example 21.

A mixture containing potassium silicofluoride by 24.4 g, magnesium oxide by 22.3 g, aluminum oxide by 11.3 g, silicon dioxide by 33.2 g and iron oxide by 8.8 g was mixed for 30 minutes in a V type mixer. Then, this mixture was placed in an alumina crucible, melted for 30 minutes at 1450° C. in electric furnace and cooled down in the furnace. Thus, 95 g of iron-containing synthetic mica was prepared. After pulverizing this mica in a ball mill for 48 hours, 90 g of this iron-containing synthetic mica powder was processed at normal temperature for 48 hours in 1 liter of aqueous solution of 0.05N hydrochloric acid while agitating. Then, it was dehydrated, rinsed and dried. Of this dried powder, 80 g was placed in an alumina crucible. Through heat treatment at 1000° C. for 10 hours in electric furnace, 75 g of synthetic mica of the present invention was obtained. The synthetic mica powder thus obtained was red in color. When measured by X-ray diffraction system RAD-B (Rigaku DenkiSha), X-ray diffraction pattern agreed well with that of synthetic mica given in FIG. 6. When iron was analyzed by ESCA, it was confirmed that iron was contained in the crystal structure.

On the synthetic mica thus prepared, L*a*b*, UV transmittance and molar numbers of iron and fluorine contained were measured by the following methods. The results are summarized in Table 4.

Measuring methods (1) Measurement of L*a*b*: 1 g of the specimen was placed in powder cell of color-difference meter (CR-200; Minolta) and measured.

(2) Measurement of UV transmittance: The specimen was added to castor oil at 20% concentration. After mixing by 3-roll mill, it was coated on a quartz plate in thickness of 10 μm. UV transmittance at 300 nm was measured using UV spectrophotometer (Shimadzu).

(3) Measurement of molar numbers of iron and fluorine contained in synthetic mica powder: Iron was measured by atomic absorption spectrophotometry, and fluorine was measured by absorption spectrophotometry.

EXAMPLE 22

Red synthetic mica of the present invention was obtained in the quantity as shown in Table 4 by the same procedure as in the Example 21, except that 24.7 g of potassium silicofluoride, 27.1 g of magnesium oxide, 5.7 g of aluminum oxide, 33.6 g of silicon dioxide and 8.9 g of iron oxide were mixed for 30 minutes by a V type mixer. When the X-ray diffraction pattern was measured by the same procedure as in the Example 21, it agreed well with that of synthetic mica. By the same procedure as in the Example 21, it was confirmed that iron was contained in the crystal structure. On the mica thus prepared, L*a*b*, UV transmittance, and molar numbers of iron and fluorine contained were measured by the same procedure as in Example 21. The results are summarized in Table 4.

EXAMPLE 23

Red synthetic mica of the present invention was obtained in the quantity shown in Table 4 by the same procedure as in the Example 21, except that the heat treatment temperature was 700° C. in Example 21. When measured by the same procedure as in Example 21 the X-ray diffraction pattern agreed well with that of synthetic mica. By the same procedure as in Example 21, it was confirmed that iron was contained in the crystal structure. On the mica thus prepared, L*a*b*, UV transmittance and molar numbers of iron and fluorine contained were measured by same procedure as in Example 21. The results are summarized in Table 4.

EXAMPLE 24

Red synthetic mica of present invention was obtained in the quantity shown in Table 4 by the same procedure as in Example 21, except that heat treatment temperature was 1200° C. and heat treatment time was 5 minutes in the Example 21. When measured by the same procedure as in Example 21, the X-ray diffraction pattern agreed well with that of synthetic mica. By the same procedure as in Example 21, it was confirmed that iron was contained in the crystal structure. On the mica thus obtained, L*a*b*, UV transmittance and molar numbers of iron and fluorine were measured as in Example 21. The results are given in Table 4.

COMPARATIVE EXAMPLE 9

Synthetic mica prepared by the same procedure as in Example 1, except that the heat treatment temperature was 1300° C. in Example 21. On the mica thus prepared, L*a*b*, UV transmittance and molar numbers of iron and fluorine contained were measured by the same procedure as in Example 21. The results are summarized in Table 4.

TABLE 4

| | | | | Results of evaluation | | | | | |
|---|---|---|---|---|---|---|---|---|---|
| | Molar number of Fe contained | F molar number | Heat treatment temperature (°C.) | External appearance | Yield (g) | L* | a* | b* | UV transmittance (%) |
| Example 21 | 0.3 | 1.9 | 1000 | Red | 75 | 65 | 11.0 | 10.2 | 58 |
| Example 22 | 0.4 | 1.9 | 1000 | Red | 73 | 68 | 8.5 | 7.3 | 61 |
| Example 23 | 0.3 | 1.94 | 700 | Red | 75 | 70 | 10.2 | 9.9 | 60 |
| Example 24 | 0.3 | 1.9 | 1200 | Red | 75 | 64 | 9.0 | 8.8 | 62 |
| Example 25 | 0.3 | 1.9 | 1000 | Red | 74 | 66 | 10.8 | 9.5 | 60 |
| Comparative Example 6 | 0 | 1.9 | 1000 | White | 70 | 90 | −1.5 | 0.0 | 99 |
| Comparative Example 7 | 0.3 | 2 | None | Whitish brown | 75 | 77 | 0.2 | 7.3 | 58 |
| Comparative Example 8 | 0.3 | 2 | 600 | Whitish Yellow | 75 | 75 | 1.1 | 7.5 | 60 |
| Comparative Example 9 | 0.3 | 1.4 | 1300 | Whitish Yellow | 74 | 75 | 1.5 | 7.3 | 90 |

EXAMPLE 25

Red synthetic mica of the present invention was obtained in the quantity as shown in Table 4 by the same procedure as in Example 21, except that 10% citric acid aqueous solution was used instead of 0.05N hydrochloric acid in Example 21. When measured by the same procedure as in Example 21, the X-ray diffraction pattern agreed well with that of synthetic mica. By the same procedure as in Example 21, it was confirmed that iron was contained in the crystal structure. On the mica thus obtained, L*a*b*, UV transmittance and molar numbers of iron and fluorine were measured as in Example 21. The results are given in Table 4.

COMPARATIVE EXAMPLE 6

25.5 g of potassium silicofluoride, 28.0 g of magnesium oxide, 11.8 g of aluminum oxide, and 34.8 g of silicon dioxide were mixed for 30 minutes in a V type mixer, and synthetic mica not containing iron was obtained by the same procedure as in the Example 21. On the mica thus prepared, L*a*b*, UV transmittance, and molar numbers of iron and fluorine contained were measured by the same procedure as in Example 21. The results are summarized in Table 4.

COMPARATIVE EXAMPLE 7

Synthetic mica was prepared by the same procedure as in Example 21 except that the heat treatment was not performed. On the mica thus prepared, L*a*b*, UV transmittance and molar numbers of iron and fluorine contained were measured by the same procedure as in Example 21. The results are summarized in Table 4.

COMPARATIVE EXAMPLE 8

Synthetic mica was prepared by the same procedure as in Example 21, except that the heat treatment temperature was 600° C. On the mica thus prepared, L*a*b*, UV transmittance and molar numbers of iron and fluorine contained were measured by the same procedure as in Example 21. The results are summarized in Table 4.

As described above, it is possible according to the present invention to an obtain excellent ultraviolet ray screening effect by the unexpected scattering effect of the mica fine particles by forming a mica fine particle layer having ultraviolet ray absorbing potency on the surface of a mica powder. Thus, the composite mica of the present invention is very useful as a base material for cosmetic products, paints, inks, coating agents, plastics, films, fibers, glasses, glazes, etc. In particular, a cosmetic product blended with the mica powder of the present invention has an excellent ultraviolet ray screening effect, a bright external color and is superb in usability and workability.

Also, it is possible according to the present invention to obtain a new synthetic mica, which has a transparent property and a light-resistant red color not found in the conventional type mica products. This is attained by coordinating a specific element at a specific position and by setting the molar number of fluorine and the molar number of iron ions within specific ranges. Because the synthetic mica of the present invention has an excellent ultraviolet ray screening effect, it can be mixed and used in cosmetic products, plastics, paints, etc. as an ultraviolet ray screening agent and without using a coloring agent. Moreover, there is no problem such as deterioration of the red color due to light. Red scale-like mica of the present invention has a color close to that of human skin and has a transparent and bright red color, and it is especially useful for the application in cosmetic products, particularly in a foundation.

What is claimed is:

1. Composite mica powder, comprising mica particles (A) with mica fine particle layer (B) formed on the surface thereof, said mica fine particle layer contains one or more types of elements selected from the group consisting of Te, Bi, Pb, Ce, Fe, Mo, Nb, W, Sb, Sn, V, Mn, Ni, Co, Zn and Ti, whereby:

covering ratio of said particles (A) by said particles (B) is lower than or equal to 1 and higher than or equal to 0.5; and ratio of particle size of said particles (B) to particle size of said particles (A) is higher than 0 and lower than or equal to 0.1, and particle size of said particle (A) is 1 to 100 μm, the particle size of particles (A) and particles (B) being determined by:

$$\text{size of particle} = \frac{\text{short axis} + \text{long axis}}{2}.$$

2. Composite mica powder according to claim 1, wherein said composite mica powder is processed by heat treatment at 700° to 1200° C.

3. An ultraviolet ray screening agent containing composite mica powder, which comprises mica particles (A) with mica fine particle layer (B) formed on the surface there, said mica fine particle layer contains one or more types of elements selected from the group consisting of Te, Bi, Pb, Ce, Fe, Mo, Nb, W, Sb, Sn, V, Mn, Ni, Co, Zn and Ti, whereby:
covering ratio of said particles (A) by said particles (B) is lower than or equal to 1 and higher than or equal to 0.5; and
ratio of particle size of said particles (B) to particle size of said particles (A) is smaller than or equal to 0.1, and particle size of said particles (A) is 1 to 100 μm, the particle size of particles (A) and particles (B) being determined by:

$$\text{size of particle} = \frac{\text{short axis} + \text{long axis}}{2}.$$

4. A red synthetic mica, expressed by the following formula (I):

$$X_{\frac{1}{2} \sim 1} Y_{2 \sim 3} (Z_4 O_{10}) F_{2 \times 0.75 \sim 2 \times 0.99} \tag{I}$$

(where X represents one or more types of ions selected from the group consisting of Na, K, Li, Ca, Rb and Sr, Y represents one or more types of ions selected from the group consisting of Mg, Fe, Ni, Mn, Al, Li, Co, Ti and Zn, Z represents one or more types of ions selected from the group consisting of Al, Si, Ge, Fe, B, Co and Ti, and at least one of Y and Z represents an iron ion), molar number of iron contained in said synthetic mica is 0.01 to 3 mols, and, when said synthetic mica is measured by powder cell method, its color is given by L*=55 to 75, a*=5 to 20, and b*=5 to 20 by the CIE 1976 (L*a*b*) space.

5. A method for manufacturing red synthetic mica according to claim 4, wherein said synthetic mica is expressed by the following formula (II):

$$X_{\frac{1}{2} \sim 1} Y_{2 \sim 3} (Z_4 O_{10}) F_2 \tag{II}$$

(where X represents one or more types of ions selected from the group consisting of Na, K, Li, Ca, Rb and Sr, Y represents one or more types of ions selected from the group consisting of Mg, Fe, Ni, Mn, Al, Li, Co, Ti and Zn, Z represents one or more types of ions selected from the group consisting of Al, Si, Ge, Fe, B, Co and Ti, and at least one of Y and Z represents an iron ion), molar number of iron contained in said synthetic mica is 0.01 to 3 mols, and said synthetic mica is processed by heat treatment at 600° to 1200° C.

6. A method for manufacturing the red synthetic mica according to claim 5, wherein synthetic mica with molar number of iron contained at 0.01 to 3 mols is treated with aqueous solution of one or more types of acids or chelating agents, and then by heat treatment at 600° to 1200° C.

7. An ultraviolet ray screening agent, containing red synthetic mica, which is expressed by the following formula (I):

$$X_{\frac{1}{2} \sim 1} Y_{2 \sim 3} (Z_4 O_{10}) F_{2 \times 0.75 \sim 2 \times 0.99} \tag{I}$$

where X represents one or more types of ions selected from the group consisting of Na, K, Li, Ca, Rb and Sr, Y represents one or more types of ions selected from the group consisting of Mg, Fe, Ni, Mn, Al, Li, Co, Ti and Zn, Z represents one or more types of ions selected from the group consisting of Al, Si, Ge, Fe, B, Co and Ti, and at least one of Y and Z represents an iron ion), molar number of iron contained in said synthetic mica is 0.01 to 3 mols, and, when said synthetic mica is measured by powder cell method, its color is given by L*=55 to 75, a*=5 to 20, and b*=5 to 20 by the CIE 1976 (L*a*b*) space.

* * * * *